United States Patent [19]

Sternlieb

[11] 4,143,423

[45] Mar. 13, 1979

[54] SURGICAL LUBRICANTS

[76] Inventor: Jack J. Sternlieb, 73-382 Salt Cedar Ave., Palm Desert, Calif. 92260

[21] Appl. No.: 844,726

[22] Filed: Oct. 25, 1977

[51] Int. Cl.² ............... A41D 19/00; A61F 13/00; C10M 3/18; C10M 1/10

[52] U.S. Cl. ...................... 2/168; 2/161 R; 2/169; 2/DIG. 7; 128/132 R; 128/294; 128/349 R; 128/350 R; 252/17; 252/18; 252/25; 427/2; 427/180

[58] Field of Search .............. 252/17, 18, 25, 41; 2/161 R, 168, 169, DIG. 7; 128/132 R, 294, 350 R, 349 R; 427/2, 180

[56] References Cited

U.S. PATENT DOCUMENTS

| | | | |
|---|---|---|---|
| 3,178,367 | 4/1965 | Dubin et al. | 252/17 |
| 3,419,110 | 12/1968 | Polti | 252/25 |
| 3,983,042 | 9/1976 | Jain et al. | 252/25 |
| 4,005,024 | 1/1977 | Rodriquez et al. | 252/17 |

OTHER PUBLICATIONS

"Handbook of Chemistry & Physics" by Weast, Chemical Rubber Co., Cleveland, Ohio, 1965, pp. 205, 206, 207, 220, 222.

*Primary Examiner*—Delbert E. Gantz
*Assistant Examiner*—Irving Vaughn
*Attorney, Agent, or Firm*—Irving B. Osofsky

[57] ABSTRACT

Plastic, natural or synthetic rubber surgical appliances such as gloves, condoms, drains, catheters and tubing are coated with a nontoxic chemical formulation to inhibit sticking during storage and to ease the installation of the device. The coating disclosed herein is a water soluble nontoxic chemical compound that incorporates Na (sodium) or K (potassium) in varying chemical combinations with carbonates, acetates, bicarbonates, acetate trihydrates and citrate dihydrate.

22 Claims, No Drawings

SURGICAL LUBRICANTS

BACKGROUND OF THE PRESENT INVENTION

Since Dr. Halstead first introduced surgical gloves so as to protect the surgeon from irritating disinfectants, patients have been adversely affected by reactions from the gloving agents. A gloving agent is a lubricating medium applied to the inside and outside of the surgeon's glove or other device to prevent sticking in storage and to help the user to install the glove, condom, drain, catheter tube or other medical device.

Water was initially used to ease the donning of rubber gloves but because it is a poor lubricant, water was abandoned as a gloving agent in the 1930's and replaced with talc powders. These talc powders in turn were found to cause severe foreign body reactions in the patients such as peritonitis, chronic fistulae and poor wound healing. By the late 1940's cornstarch was substituted for talc. In 1956 the first cases of starch peritonitis in humans were described in numerous reports. In the 1960's glove manufacturers introduced a rice starch derivative hoping that it would cause fewer problems but it was quickly removed from the market when it was associated with an increased incidence of peritonitis. Presently, throughout the world, most commercially available surgical gloves contain a cornstarch derivative for lubrication. Gloving powders, lotions and creams also generally contain cornstarch. Cases of pelvic peritonitis have been reported following the repeated use of condoms which contained starch powder. Starch may be responsible for extraperitoneal inflammatory reactions and the postpericardiotomy syndrome.

Although the medical profession understands that talc and starch lubricants cause severe reactions and the issue is discussed in many United States patents such as U.S. Pat. Nos. 3,728,739 and 3,872,515, the commercially available gloves, condoms, drains, catheters and tubes utilize starch in some form as a lubricant coating. On the other hand, the coating disclosed herein is readily absorbed by tissue without deleterious reactions.

SUMMARY OF THE PRESENT INVENTION

The subject invention is a lubricating coating which can be used on the surfaces of surgical gloves, condoms, drains, catheters, tubes and other devices intended to be inserted into the human body or into animals. The coating acts as a lubricant to facilitate the installation of said medical devices and also acts to prevent the rubber, synthetic rubber and/or plastic items from adhering to each other or sticking together during storage. The coating also acts to inhibit growth of bacteria or mold.

Experiments conducted by the inventor and described in a paper presented by him at the Eighty-fourth Annual Meeting of the Western Surgical Association at Coronado, California on November 16, 1976 have shown that there were no adverse reactions in animals or patients and that one patient who had a previous episode of starch peritonitis had no reaction from surgical gloves treated with sodium bicarbonate as a gloving agent. The lubricant was applied to the glove by shaking a layer of sodium bicarbonate, from a perforated can, over the entire inner and outer surface so as to completely obscure the uncoated surface. Depth of the loose powder, which typically can be 1/16th inch thick, is unimportant so long as the entire device is covered. The glove is then held up and shaken so that most of the loose powder falls off leaving a thin film which adheres to the surface of the rubber or plastic material. The thickness of this film is not important and is dependent on the fineness of the sodium bicarbonate used and on the "stickiness" of the gloves. Sufficient powder remains to prevent self-adherence and to ease installation of the glove. It is self-regulating in that gloves with tacky surfaces cause powder to remain as required.

The gloving agent which is another name for the lubricant may be installed on and in the gloves and surgical devices by techniques presently in use in the industry and known by those skilled in the art. This invention does not disclose or claim the technique for installing the lubricant. This invention involves the discovery that certain alkali metal compounds may be coated on the surfaces of surgical appliances by conventional means where they act as lubricants and gloving agents which are nontoxic and which do not cause adverse reactions in animals or human patients. For example, it may be installed as a powder by dusting the items to be coated or it may be deposited by evaporating an aqueous solution containing the lubricant on the surface of the item to be coated. Sodium bicarbonate is the preferred embodiment. Other nontoxic lubricating coatings of the present invention which may be used to ease installation and to prevent self-adhesion in the storage of plastic, natural or synthetic rubber surgical appliances such as gloves, condoms, drains, catheters and tubing to which said coatings are applied to the surfaces thereof, consist of coatings of a chemical compound of one alkali metal selected from the group consisting of sodium (Na) and potassium (K) in chemical combination with a radical selected from the group consisting of carbonate ($CO_3$), bicarbonate ($HCO_3$), acetate ($C_2H_3O_2$), acetate trihydrate ($C_2H_3O_2.3H_2O$), and citrate dihydrate ($C_6H_5O_7.2H_2O$). Examples of other chemical compounds which may be used as the nontoxic lubricating coatings of the present invention include sodium carbonate ($Na_2CO_3$), sodium bicarbonate ($NaHCO_3$), sodium citrate dihydrate ($Na_3C_6H_5O_7.2H_2O$), sodium acetate ($NaC_2H_3O_2$), sodium acetate trihydrate ($NaC_2H_3O_2.3H_2O$), potassium carbonate ($K_2CO_3$), potassium bicarbonate ($KHCO_3$), potassium citrate dihydrate ($K_3C_6H_5O_7.2H_2O$) and potassium acetate ($KC_2H_3O_2$).

Although sodium bicarbonate is discussed herein as the lubricating agent, for exemplary purposes, it is to be understood that such an embodiment is merely illustrative of and not restrictive on the broad invention and that we do not desire to be limited in our invention to the specific arrangement described because various other obvious combinations and/or modifications may occur to persons having ordinary skill in the art.

What is claimed is:

1. The process of applying to plastic, natural or synthetic rubber surgical devices a nontoxic lubricating coating which does not cause adverse reactions in animals or human patients, which eases installation, and which prevents self-adhesion in storage of said devices, which comprises: coating the surfaces of said devices with a dry coating which consists of a chemical compound of one alkali metal selected from the group consisting of sodium (Na) and potassium (K) in chemical combination with a radical selected from the group consisting of carbonate ($CO_3$), bicarbonate ($HCO_3$), acetate ($C_2H_3O_2$), acetate trihydrate ($C_2H_3O_2.3H_2O$), and citrate dihydrate ($C_6H_5O_7.2H_2O$).

2. The process of claim 1 wherein the coating is sodium carbonate ($Na_2CO_3$).

3. The process of claim 1 wherein the coating is sodium bicarbonate ($NaHCO_3$).

4. The process of claim 1 wherein the coating is sodium citrate, dihydrate ($Na_3C_6H_5O_7.2H_2O$).

5. The process of claim 1 wherein the coating is sodium acetate ($NaC_2H_3O_2$).

6. The process of claim 1 wherein the coating is sodium acetate, trihydrate ($NaC_2H_3O_2.3H_2O$).

7. The process of claim 1 wherein the coating is potassium carbonate ($K_2CO_3$).

8. The process of claim 1 wherein the coating is potassium bicarbonate ($KHCO_3$).

9. The process of claim 1 wherein the coating is potassium citrate, dihydrate ($K_3C_6H_5O_7.2H_2O$).

10. The process of claim 1 wherein the coating is potassium acetate ($KC_2H_3O_2$).

11. The process of claim 1 wherein the coating is potassium acetate, trihydrate ($KC_2H_3O_2.3H_2O$).

12. Plastic, natural or synthetic rubber surgical devices whose surfaces are coated with a dry layer of a chemical compound of one alkali metal selected from the group consisting of sodium (Na) and potassium (K) in chemical combination with a radical selected from the group consisting of carbonate ($CO_3$), bicarbonate ($HCO_3$), acetate ($C_2H_3O_2$), acetate trihydrate ($C_2H_3O_2.3H_2O$), and citrate dihydrate ($C_6H_5O_7.2H_2O$) as a nontoxic lubricating coating to ease installation and to prevent self-adhesion in storage.

13. The coated surgical devices of claim 12 wherein the coating is sodium carbonate ($Na_2CO_3$).

14. The coated surgical devices of claim 12 wherein the coating is sodium bicarbonate ($NaHCO_3$).

15. The coated surgical devices of claim 12 wherein the coating is sodium citrate, dihydrate ($Na_3C_6H_5O_7.2H_2O$).

16. The coated surgical devices of claim 12 wherein the coating is sodium acetate ($NaC_2H_3O_2$).

17. The coated surgical devices of claim 12 wherein the coating is sodium acetate, trihydrate ($NaC_2H_3O_2.3H_2O$).

18. The coated surgical devices of claim 12 wherein the coating is potassium carbonate ($K_2CO_3$).

19. The coated surgical devices of claim 12 wherein the coating is potassium bicarbonate ($KHCO_3$).

20. The coated surgical devices of claim 12 wherein the coating is potassium citrate, dihydrate ($K_3C_6H_5O_7.2H_2O$).

21. The coated surgical devices of claim 12 wherein the coating is potassium acetate ($KC_2H_3O_2$).

22. The coated surgical devices of claim 12 wherein the coating is potassium acetate, trihydrate ($KC_2H_3O_2.3H_2O$).

* * * * *